(12) United States Patent
Okada

(10) Patent No.: US 7,946,978 B2
(45) Date of Patent: May 24, 2011

(54) ENDOSCOPE TREATMENT TOOL INSERTION-EXTRACTION SYSTEM

(75) Inventor: Tsutomu Okada, Tokyo (JP)

(73) Assignee: Olympus Corporation, Tokyo (JP)

( * ) Notice: Subject to any disclaimer, the term of this patent is extended or adjusted under 35 U.S.C. 154(b) by 418 days.

(21) Appl. No.: 11/777,782

(22) Filed: Jul. 13, 2007

(65) Prior Publication Data

US 2008/0015410 A1   Jan. 17, 2008

Related U.S. Application Data

(63) Continuation of application No. 10/986,125, filed on Nov. 10, 2004, now Pat. No. 7,582,054.

(30) Foreign Application Priority Data

Nov. 28, 2003   (JP) ................................. 2003-398831
Jan. 17, 2007   (JP) ................................. 2007-008294

(51) Int. Cl.
*A61B 1/00*   (2006.01)

(52) U.S. Cl. ......................... 600/106; 600/104; 600/107

(58) Field of Classification Search .................. 600/104, 600/106, 118, 131, 132, 153–159
See application file for complete search history.

(56) References Cited

U.S. PATENT DOCUMENTS

| | | | |
|---|---|---|---|
| 2,711,734 A | 6/1955 | Moe | |
| 3,835,854 A | 9/1974 | Jewett | |
| 4,402,313 A * | 9/1983 | Yabe | 600/132 |
| 4,616,648 A * | 10/1986 | Simpson | 606/108 |
| 5,174,276 A * | 12/1992 | Crockard | 600/104 |
| 5,346,498 A | 9/1994 | Greelis et al. | |
| 5,376,094 A | 12/1994 | Kline | |
| 5,431,645 A * | 7/1995 | Smith et al. | 606/1 |
| 5,540,649 A | 7/1996 | Bonnell et al. | |
| 5,695,491 A | 12/1997 | Silverstein | |
| 5,779,623 A | 7/1998 | Bonnell | |
| 5,882,294 A | 3/1999 | Storz et al. | |
| 5,931,833 A | 8/1999 | Silverstein | |
| 6,074,402 A * | 6/2000 | Peifer et al. | 606/139 |
| 6,171,234 B1 | 1/2001 | White et al. | |
| 6,358,199 B1 | 3/2002 | Pauker et al. | |
| 6,520,954 B2 * | 2/2003 | Ouchi | 606/1 |
| 6,569,084 B1 * | 5/2003 | Mizuno et al. | 600/102 |
| 6,626,824 B2 | 9/2003 | Ruegg et al. | |
| 6,726,675 B1 * | 4/2004 | Beyar | 604/510 |

(Continued)

FOREIGN PATENT DOCUMENTS

JP   S57-117823   7/1982

(Continued)

*Primary Examiner* — Matthew J Kasztejna
(74) *Attorney, Agent, or Firm* — Scully, Scott, Murphy & Presser, P.C.

(57) ABSTRACT

This endoscope treatment tool insertion-extraction system is provided with: a first treatment tool and a second treatment tool which are insertable into and retractable from a forceps channel of an endoscope; a first insertion-extraction mechanism which feeds the first treatment tool into the forceps channel or removes the first treatment tool from the forceps channel; a second insertion-extraction mechanism which feeds the second treatment tool into the forceps channel or removes the second treatment tool from the forceps channel; one driving section which drives the first insertion-extraction mechanism and the second insertion-extraction; and a selection section which selectively engage the driving section with one of the first insertion-extraction mechanism and the second insertion-extraction mechanism.

18 Claims, 4 Drawing Sheets

U.S. PATENT DOCUMENTS

| | | |
|---|---|---|
| 7,118,582 B1 | 10/2006 | Wang et al. |
| 7,179,223 B2 | 2/2007 | Motoki et al. |
| 7,294,135 B2 * | 11/2007 | Stephens et al. .............. 606/108 |
| 2001/0004676 A1 * | 6/2001 | Ouchi ........................... 600/106 |
| 2003/0176770 A1 * | 9/2003 | Merril et al. .................. 600/118 |
| 2005/0041889 A1 | 2/2005 | Scarberry |
| 2006/0287574 A1 | 12/2006 | Chin |

FOREIGN PATENT DOCUMENTS

| | | |
|---|---|---|
| JP | S57-136431 | 8/1982 |
| JP | S57-190541 | 11/1982 |
| JP | 2000-000207 | 1/2000 |

* cited by examiner

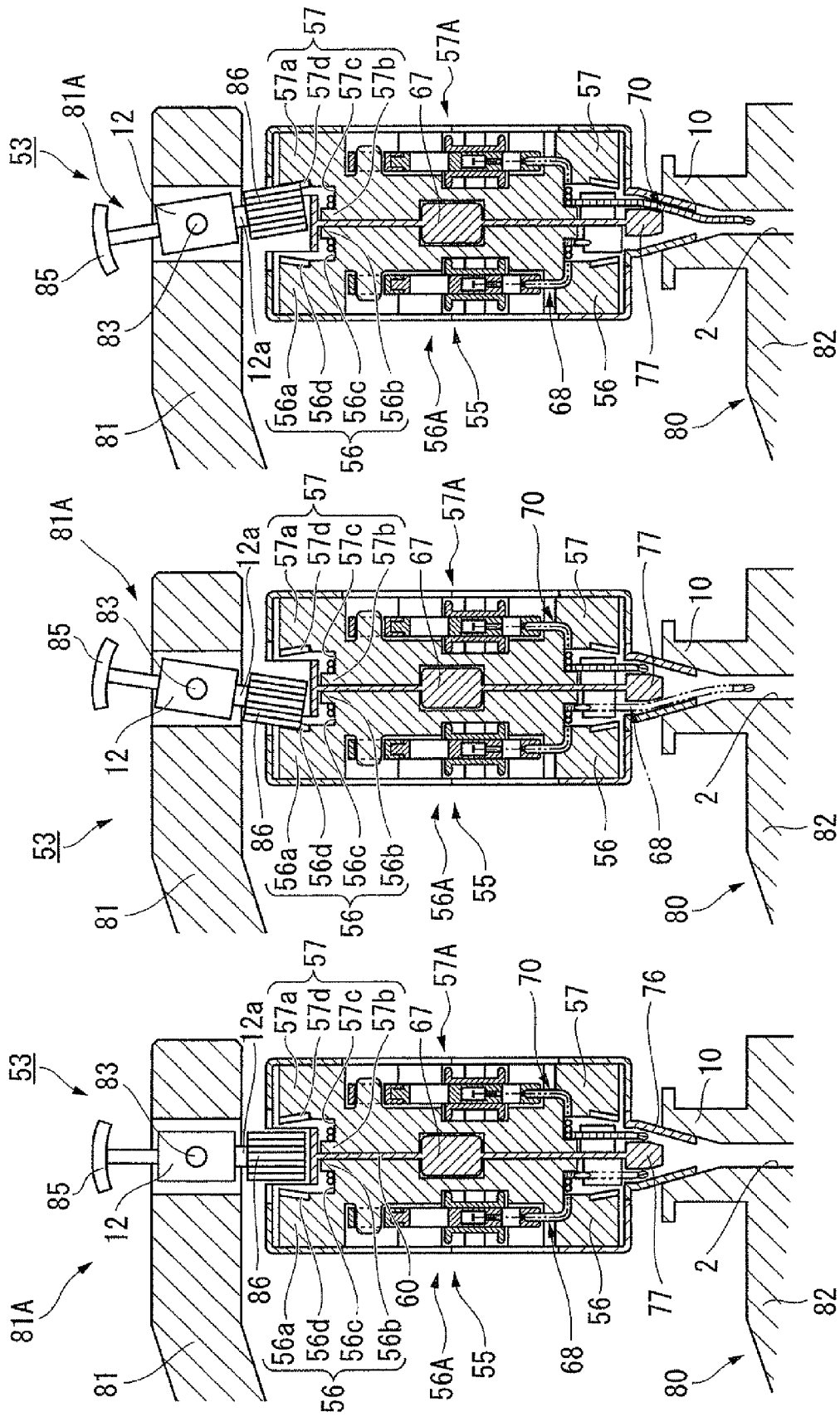

US 7,946,978 B2

ENDOSCOPE TREATMENT TOOL INSERTION-EXTRACTION SYSTEM

This application is a Continuation Application of U.S. patent application Ser. No. 10/986,125, filed on Nov. 10, 2004.

Priority is claimed on Japanese Patent Application No. 2003-398831, filed on Nov. 28, 2003, and Japanese Patent Application No. 2007-8294, filed Jan. 17, 2007, the contents of which are incorporated herein by reference.

BACKGROUND OF THE INVENTION

1. Field of the Invention

The present invention relates to an endoscope treatment tool insertion-extraction system for automatically inserting and extracting a treatment tool, such as a forceps, a catheter, or a high frequency knife, that is inserted into a body cavity through a forceps channel of an endoscope.

2. Description of the Related Art

Conventionally, when a treatment tool such as a forceps is inserted into a body cavity through a forceps channel of an endoscope, an operator inserts it into the forceps channel while holding the treatment tool in his/her own hand. For example, since the total length of an endoscope for use with the colon can be as long as 2 m, an endoscope provided with an insertion-extraction apparatus that inserts and extracts a treatment tool that is inserted from the treatment tool insertion opening of the endoscope has been proposed, in order to reduce the labor of the treatment tool insertion operation (for example, refer to FIG. 1 of Japanese Unexamined Patent Application, First Publication No. S57-117823).

Moreover, an insertion-extraction apparatus that houses and retains a plurality of treatment tools in individual housing sections has also been proposed (for example, refer to FIGS. 1, 3, 6 and 7 of Japanese Unexamined Patent Application, First Publication No. 2000-207).

SUMMARY OF THE INVENTION

An endoscope treatment tool insertion-extraction system of the present invention is provided with: a first treatment tool and a second treatment tool which are insertable into and retractable from a forceps channel of an endoscope; a first insertion-extraction mechanism which feeds the first treatment tool into the forceps channel or removes the first treatment tool from the forceps channel; a second insertion-extraction mechanism which feeds the second treatment tool into the forceps channel or removes the second treatment tool from the forceps channel; one driving section which drives the first insertion-extraction mechanism and the second insertion-extraction; and a selection section which selectively engage the driving section with one of the first insertion-extraction mechanism and the second insertion-extraction mechanism.

The endoscope treatment tool insertion-extraction system may be further provided with a treatment tool unit provided with the first treatment tool, the second treatment tool, the first insertion-extraction mechanism, and the second insertion-extraction mechanism.

The selection section may be rotatable such that the driving section be engageable with the first insertion-extraction mechanism or the second insertion-extraction mechanism.

The driving section may be provided in the endoscope.

A driving power source of the driving section may be built in a light source apparatus which is connected to the endoscope.

A driving power source of the driving section may be built in an operation section of the endoscope.

The driving section may include a motor.

BRIEF DESCRIPTION OF THE DRAWINGS

FIG. 3A is a cross-sectional view of the treatment tool unit taking along the line G-G of FIG. 2, while FIG. 3B is another cross-sectional view of the treatment tool unit taking along the line H-H of FIG. 2.

FIGS. 5A to 5C are cross-sectional views of the treatment tool unit in operation.

DETAILED DESCRIPTION OF THE INVENTION

Figure 1:
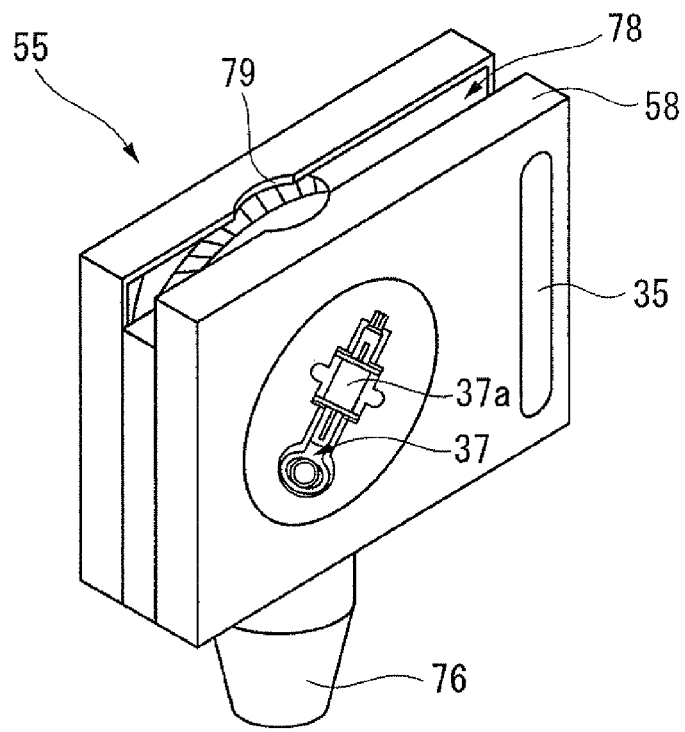
FIG. 1 is a perspective view of a treatment tool unit according to one embodiment of the present invention.
Figure 2:
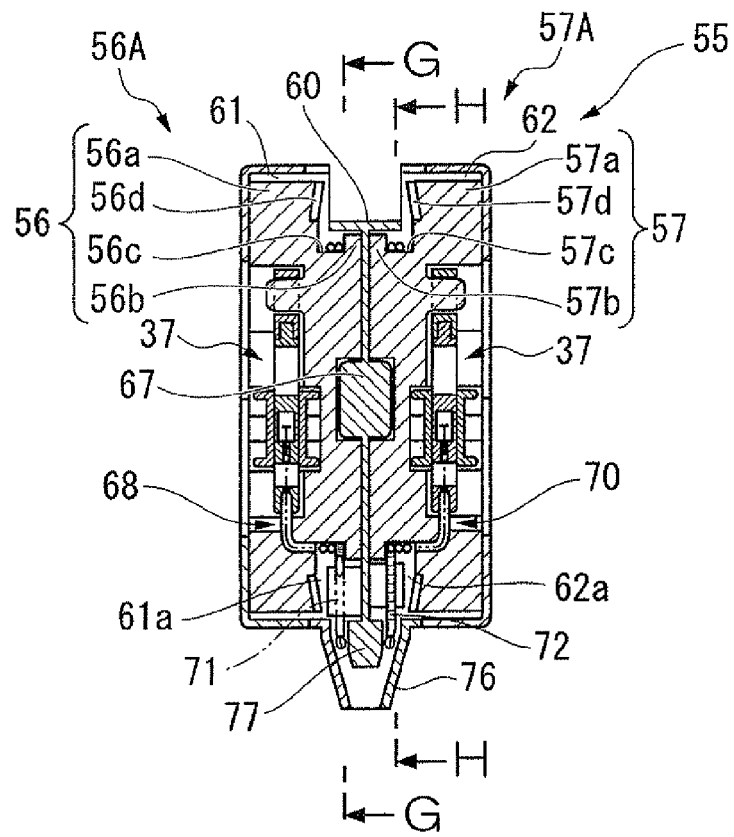
FIG. 2 is a cross-sectional view of the treatment tool unit.
Figure 3:
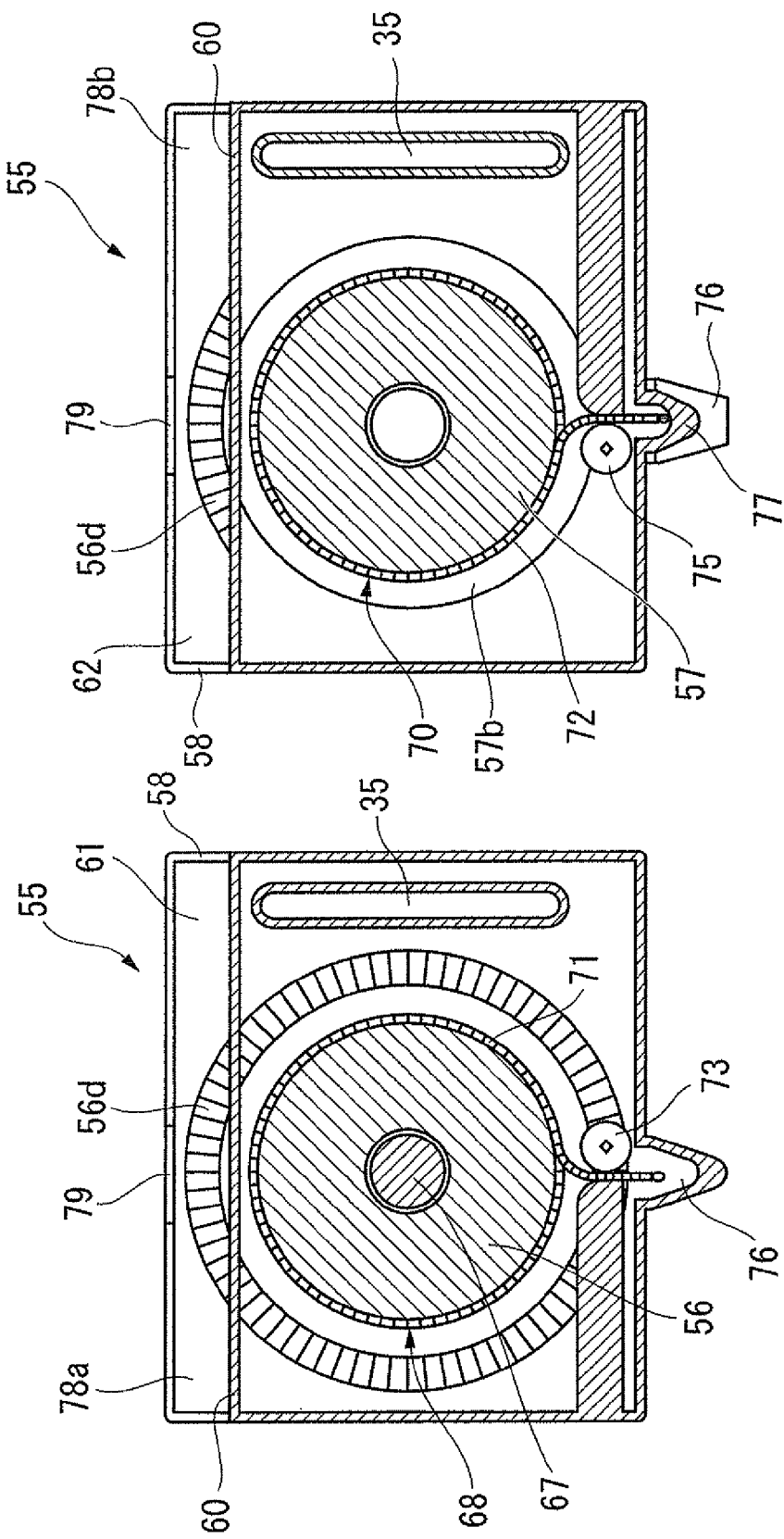

One embodiment of an endoscope treatment tool insertion-extraction system of the present invention will be explained below with reference to FIGS. 1 to 5C.

An endoscope treatment tool insertion-extraction system 53 of the present embodiment is provided with a treatment tool unit 55.

The treatment tool unit 55 is provided with a first insertion-extraction mechanism 56A, a second insertion-extraction mechanism 57A, and a cassette 58 accommodating these. The first insertion-extraction mechanism 56A includes a bobbin 56, while the second insertion-extraction mechanism 57A includes a bobbin 57.

The cassette 58 includes two compartments 61 and 62 which are separated by a partition 60. The bobbins 56 and 57 are respectively and rotatably supported on a protrusion 67 formed on the partition 60 so as to project toward the inside of each compartments 61 and 62.

The bobbin 56 has a large-diameter section 56a on the one end thereof and a small-diameter section 56b on another end thereof while the bobbin 57 has a large-diameter section 57a on the one end thereof and a small-diameter section 57b on another end thereof. Furthermore, a winding section 56c having smaller diameter than that of the small-diameter section 56b is formed between the large-diameter section 56a and the small-diameter section 56b, while a winding section 57c having smaller diameter than that of the small-diameter section 57b is formed between the large-diameter section 57a and the small-diameter section 57b.

Teeth 56d is formed in a corrugated manner on an inside face on the circumference of the large-diameter section 56a, while teeth 57d is formed in a corrugated manner on an inside face on the circumference of the large-diameter section 57a.

The teeth 56d and 57d are disposed so as to oppose with each other. An insertion section 71 of a first forceps (a first treatment tool) 68 is wound around the winding section 56c, while an insertion section 72 of a second forceps (a second treatment tool) 70 is wound around the winding section 57c. These first forceps 68 and the second forceps 70 are wound in the opposite directions to each other.

Portions near the distal ends of the insertion sections 71 and 72 are arranged so as to direct a treatment tool portal 76 that is connected to a lower portion of the cassette 58, by rollers 73 and 75 rotatably provided in the lower portion of the cassette 58. Forceps operating sections 37 connected to bottom ends of the insertion sections 71 and 72 of the first forceps 68 and the second forceps 70, are provided with sliders 37a which are arranged on the sides of the small-diameter sections 56b and 57b of the bobbins 56 and 57 so as to be exposed to the outside of the cassette 58.

A separator 77 that extends downward from the partition 60 of the cassette 58 is arranged in the treatment tool portal 76. Exits 61a and 62a of the respective compartments 61 and 62 merge at the below of the separator 77.

A groove 78 is formed in the upper part of the cassette 58. Side faces 78a and 78b, which form a part of the groove 78, are opened so as to expose a part of the teeth 56d and 57d. In addition, a motor swivel hole 79 is formed in the groove 78.

An endoscope 80 to which the treatment unit 55 of the endoscope treatment tool insertion-extraction system 53 is to be connected, is provided with an operating section 82 having an engaging portion 81 which supports a motor (driving section) 12 that is arranged so as to be engageable with the treatment tool unit 55. The operating section 82 has a forceps opening 10 that communicates with the forceps channel 2. A connection part 81 is arranged above the forceps opening 10 so as to have a predetermined distance therefrom for arranging the treatment tool unit 55.

The connection part 81 includes a selection mechanism 81A which selects one of the first forceps 68 and the second forceps 70, and inserts and extracts it. The selection mechanism 81A is provided with: the motor 12; a rotational shaft 12a of the motor 12; a pin 83 which pivots the motor 12 so as to swivel freely about the axis of the forceps opening 10; a knob 85 provided at the end part of the motor 12; and a motor gear 86, which meshes with the teeth 56d of the first insertion-extraction mechanism 56A and the teeth 57d of the second insertion-extraction mechanism 57A, and which is provided at the distal end of the rotational shaft 12a of the motor 12.

The operating section 82 is connected via a universal cord 15 to a light source apparatus 13 that supplies light to the endoscope 80. The motor 12 is connected via a wiring 17 in the universal cord 15 to a motor driving power source 16 (a driving power source) provided in the light source apparatus 13. Moreover, the motor driving power source 16 may be a battery housed in the operating section 82, or the like.

The operating section 82 is provided with, for example, a first switch 18 that rotates clockwise or stops the motor 12, and a second switch 20 that rotates counterclockwise or stops the motor 12. These switches 18 and 20 turn ON when pressed, and rotate the motor 12 in the clockwise rotational direction or the counterclockwise rotational direction, and stop the motor 12 when released.

Next, an operation method of the endoscope treatment tool insertion-extraction system 53 of the present embodiment will be explained below.

Figure 4:
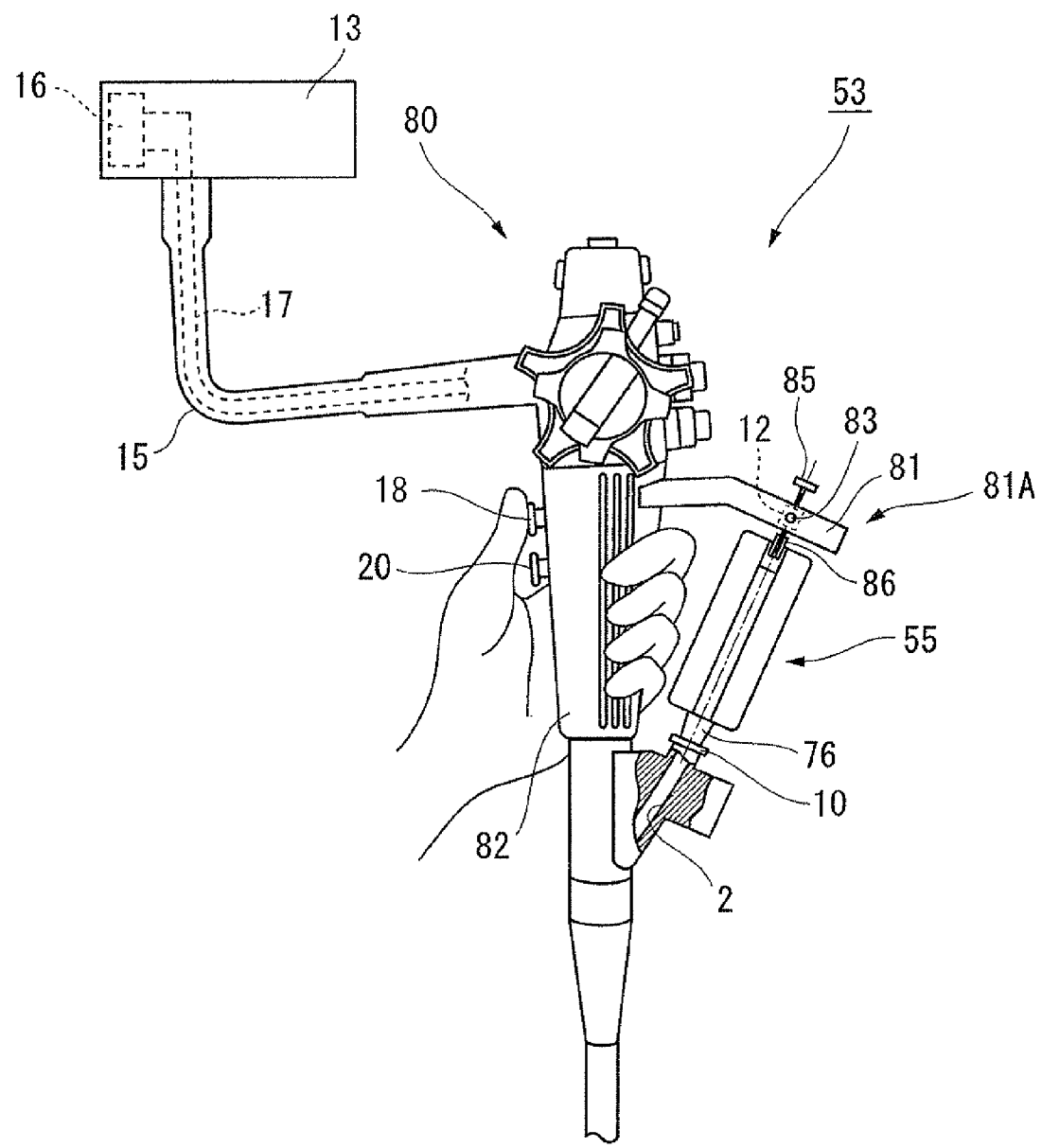
FIG. 4 is an explanatory view showing an operation method of the endoscope treatment tool insertion-extraction system according to one embodiment of the present invention.

After inserting the endoscope 80 into a body cavity, the treatment tool portal 76 of the treatment tool unit 55 is attached to the forceps opening 10 as shown in FIG. 4. Furthermore, the motor gear 86 of the motor 12 is inserted into the motor swivel hole 79 of the treatment tool unit 55. In this way, the treatment tool unit 55 is attached to the endoscope 80 as shown in the FIG. 5A.

Next, as shown in FIG. 5B, when the first forceps 68 is used, the knob 85 of the motor 12, which is the selection mechanism 81A, is inclined to the right. Then, the motor 12 swivels about the pin 83, and the motor gear 86 meshes with the teeth 56d of one bobbin 56 of the treatment tool unit 55.

At this time, if the first switch 18 of the endoscope 80 is pressed, then the motor 12 rotates clockwise for example, and the motor gear 86 transmits the rotational force to the teeth 56d, and the bobbin 56 rotates clockwise in FIG. 3A. As a result, the first forceps 68 is inserted into the forceps channel 2 of the endoscope 80.

When the treatment tool 68 has reached an appropriate position while observing with the endoscope 80, by releasing the first switch 18 of the endoscope 80 to stop the rotation of the motor 12, the movement of the first forceps 68 is stopped. Opening and closing operations of the first forceps 68 is performed by removing the forceps operating sections 37 from the bobbin 56.

When extracting the first forceps 68, the motor 12 is rotated in the opposite direction (counterclockwise rotational direction) by pressing the second switch 20 of the endoscope 80. As a result, the bobbin 56 rotates in the opposite rotational direction by an operation opposite to that for insertion, and the insertion section 71 of the first forceps 68 is wound onto the bobbin 56. When the insertion section 71 is extracted from the forceps channel 2 of the endoscope 80, the second switch 20 is released and the motor 12 is stopped.

Next, the second forceps 70 is inserted. As shown in the FIG. 5C, when the knob 85 of the selection mechanism 81A is operated so as to incline to the left, the motor 12 swivels about the pin 83, and the motor gear 86 meshes with the teeth 57d of the other bobbin 57 of the treatment tool unit 55.

Then, when the first switch 18 of the endoscope 80 is pressed, the motor 12 rotates clockwise for example, and the motor gear 86 transmits rotational force to the teeth 57d, and the bobbin 57 rotates counterclockwise in FIG. 3B. As a result, the second forceps 70 is inserted into the forceps channel 2 of the endoscope 80.

While observing with the endoscope 80, when the second forceps 70 has reached an appropriate position, movement of the second forceps 70 is stopped by releasing the first switch 18 of the endoscope 80 to stop rotation of the motor 12. The operation of the second forceps 70 is similar to that of the first forceps 68.

In order to extract the second forceps 70 from the forceps channel 2, as same as the case of the first forceps 68, the motor 12 is moved to the center after removing the second forceps 70 from the forceps channel 2, to detach the treatment tool unit 55 from the endoscope 80.

As has been explained in the above, the present invention employed the endoscope treatment tool insertion-extraction system provided with: a first treatment tool and a second treatment tool which are insertable into and retractable from a forceps channel of an endoscope; a first insertion-extraction mechanism which feeds the first treatment tool into the forceps channel or removes the first treatment tool from the forceps channel; a second insertion-extraction mechanism which feeds the second treatment tool into the forceps channel or removes the second treatment tool from the forceps channel; one driving section which drives the first insertion-extraction mechanism and the second insertion-extraction; and a selection section which selectively engage the driving section with one of the first insertion-extraction mechanism and the second insertion-extraction mechanism.

According to the endoscope treatment tool insertion-extraction system of the present embodiment, two treatment tools can be inserted and extracted selectively and easily through one forceps channel. At this time, one of the treatment tools can be selected to be inserted and retracted. In addition, when the treatment tools are inserted into and extracted from the forceps channel, the treatment tools need not be supported by hand; therefore, the possibility of applying excessive load onto the treatment tools due to hand-operations can be further reduced. Accordingly, insertion and extraction of the treatment tools can be easily carried out.

Accordingly, since the treatment tool unit is connected to the endoscope, the treatment tool need no longer be supported when inserting and extracting the treatment tool, so that the treatment tool no longer gets damaged. Therefore, insertion and extraction of the treatment tool can be made easier, and it can be manufactured compactly and inexpensively. Furthermore, it becomes possible for the operator who operates the endoscope to also operate the treatment tool.

While a preferred embodiment of the invention has been described and illustrated above, it should be understood that this is an exemplary of the invention and is not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope treatment tool insertion-extraction system comprising:
   a first treatment tool and a second treatment tool which are insertable into and retractable from a forceps channel of an endoscope;
   a first insertion-extraction mechanism which feeds the first treatment tool into the forceps channel or removes the first treatment tool from the forceps channel;
   a second insertion-extraction mechanism which feeds the second treatment tool into the forceps channel or removes the second treatment tool from the forceps channel;
   one common driving section which is engageable with and drives the first insertion-extraction mechanism or the second insertion-extraction; and
   a selection section which selectively engages the driving section with one of the first insertion-extraction mechanism and the second insertion-extraction mechanism
   wherein a driving power source of the driving section is built in a light source apparatus which is connected to the endoscope.

2. The endoscope treatment tool insertion-extraction system according to claim 1, further comprising a treatment tool unit provided with the first treatment tool, the second treatment tool, the first insertion-extraction mechanism, and the second insertion-extraction mechanism.

3. The endoscope treatment tool insertion-extraction system according to claim 2, wherein the treatment unit is removable from the endoscope.

4. The endoscope treatment tool insertion-extraction system according to claim 1, wherein the selection section is rotatable such that the driving section be engageable with the first insertion-extraction mechanism or the second insertion-extraction mechanism.

5. The endoscope treatment tool insertion-extraction system according to claim 1, wherein the driving section is provided in the endoscope.

6. The endoscope treatment tool insertion-extraction system according to claim 1, further comprising a system for selectively feeding the first treatment tool or the second treatment tool into the forceps channel.

7. An endoscope treatment tool insertion-extraction system comprising:
   a first treatment tool and a second treatment tool which are insertable into and retractable from a forceps channel of an endoscope;
   a first insertion-extraction mechanism which feeds the first treatment tool into the forceps channel or removes the first treatment tool from the forceps channel;
   a second insertion-extraction mechanism which feeds the second treatment tool into the forceps channel or removes the second treatment tool from the forceps channel;
   one common driving section which is engageable with and drives the first insertion-extraction mechanism or the second insertion-extraction; and
   a selection section which selectively engages the driving section with one of the first insertion-extraction mechanism and the second insertion-extraction mechanism
   wherein a driving power source of the driving section is built in an operation section of the endoscope.

8. The endoscope treatment tool insertion-extraction system according to claim 7, further comprising a treatment tool unit provided with the first treatment tool, the second treatment tool, the first insertion-extraction mechanism, and the second insertion-extraction mechanism.

9. The endoscope treatment tool insertion-extraction system according to claim 8, wherein the treatment unit is removable from an endoscope.

10. The endoscope treatment tool insertion-extraction system according to claim 7, wherein the selection section is rotatable such that the driving section be engageable with the first insertion-extraction mechanism or the second insertion-extraction mechanism.

11. The endoscope treatment tool insertion-extraction system according to claim 7, wherein the driving section is provided in the endoscope.

12. The endoscope treatment tool insertion-extraction system according to claim 7, further comprising a system for selectively feeding the first treatment tool or the second treatment tool into the forceps channel.

13. An endoscope treatment tool insertion-extraction system comprising:
   a first treatment tool and a second treatment tool which are insertable into and retractable from a forceps channel of an endoscope;
   a first insertion-extraction mechanism which feeds the first treatment tool into the forceps channel or removes the first treatment tool from the forceps channel;
   a second insertion-extraction mechanism which feeds the second treatment tool into the forceps channel or removes the second treatment tool from the forceps channel;
   one common driving section which is engageable with and drives the first insertion-extraction mechanism or the second insertion-extraction; and
   a selection section which selectively engages the driving section with one of the first insertion-extraction mechanism and the second insertion-extraction mechanism
   wherein the driving section comprises a motor.

14. The endoscope treatment tool insertion-extraction system according to claim 13, further comprising a treatment tool unit provided with the first treatment tool, the second treatment tool, the first insertion-extraction mechanism, and the second insertion-extraction mechanism.

15. The endoscope treatment tool insertion-extraction system according to claim 14, wherein the treatment unit is removable from an endoscope.

16. The endoscope treatment tool insertion-extraction system according to claim 13, wherein the selection section is rotatable such that the driving section be engageable with the first insertion-extraction mechanism or the second insertion-extraction mechanism.

17. The endoscope treatment tool insertion-extraction system according to claim 13, wherein the driving section is provided in the endoscope.

18. The endoscope treatment tool insertion-extraction system according to claim 13, further comprising a system for selectively feeding the first treatment tool or the second treatment tool into the forceps channel.

* * * * *